United States Patent [19]

Hamann

[11] Patent Number: 5,067,092
[45] Date of Patent: Nov. 19, 1991

[54] PRESPOT DETECTION METHOD AND APPARATUS IN AN ANALYZER

[75] Inventor: J. Eric Hamann, Spencerport, N.Y.

[73] Assignee: Eastman Kodak Company, Rochester, N.Y.

[21] Appl. No.: 469,860

[22] Filed: Jan. 24, 1990

[51] Int. Cl.$^5$ .................. G01N 35/00; G01N 33/18
[52] U.S. Cl. .................... 364/496; 364/497; 436/46
[58] Field of Search ........... 364/496, 497, 498, 413.08, 364/413.1; 250/306, 307, 390.04; 356/244, 246, 39, 436, 440; 436/46, 44, 39, 164; 422/63, 66, 67, 100

[56] References Cited

U.S. PATENT DOCUMENTS

| 4,513,438 | 4/1985 | Graham et al. | 364/413.08 |
| 4,523,278 | 6/1985 | Reinhardt et al. | 364/413.1 |
| 4,702,595 | 10/1987 | Mutschler et al. | 364/413.08 |
| 4,852,025 | 7/1989 | Herpichböhm | 364/497 |
| 4,959,796 | 9/1990 | Hidaka et al. | 364/497 |

Primary Examiner—Parshotam S. Lall
Assistant Examiner—Ellis B. Ramirez
Attorney, Agent, or Firm—Dana M. Schmidt

[57] ABSTRACT

A method and apparatus for detecting an erroneous pre-spotting of liquid onto a test element in an analyzer. The invention utilizes a wetness detector and calculates the estimated second derivative of the R-C time decay curve produced by such a detector, to determine if a sudden increase in a slope exceeds more than a threshold value for two consecutive points. The threshold value is picked so as to exceed sudden increases that can be created by noise in the system.

5 Claims, 7 Drawing Sheets

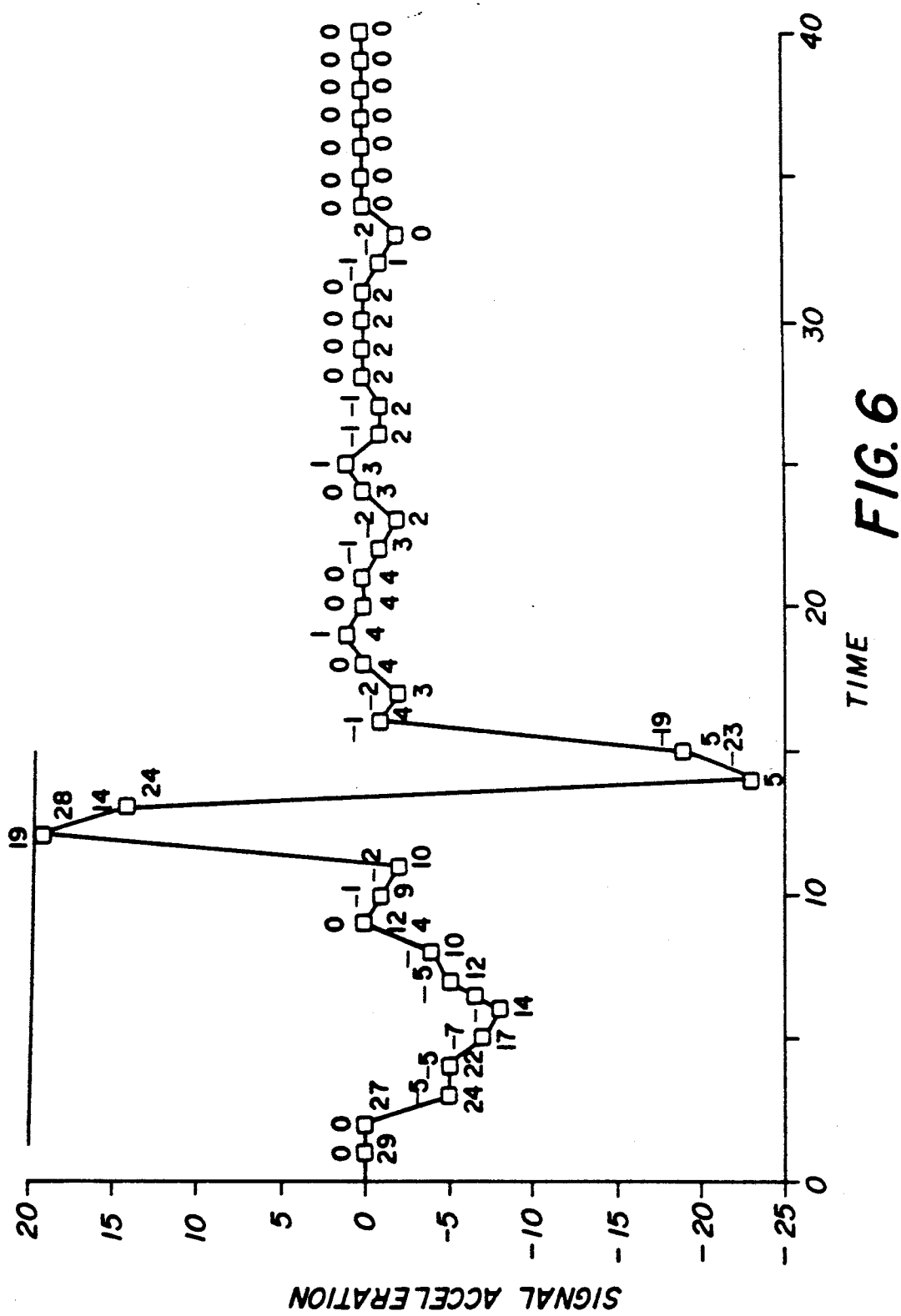

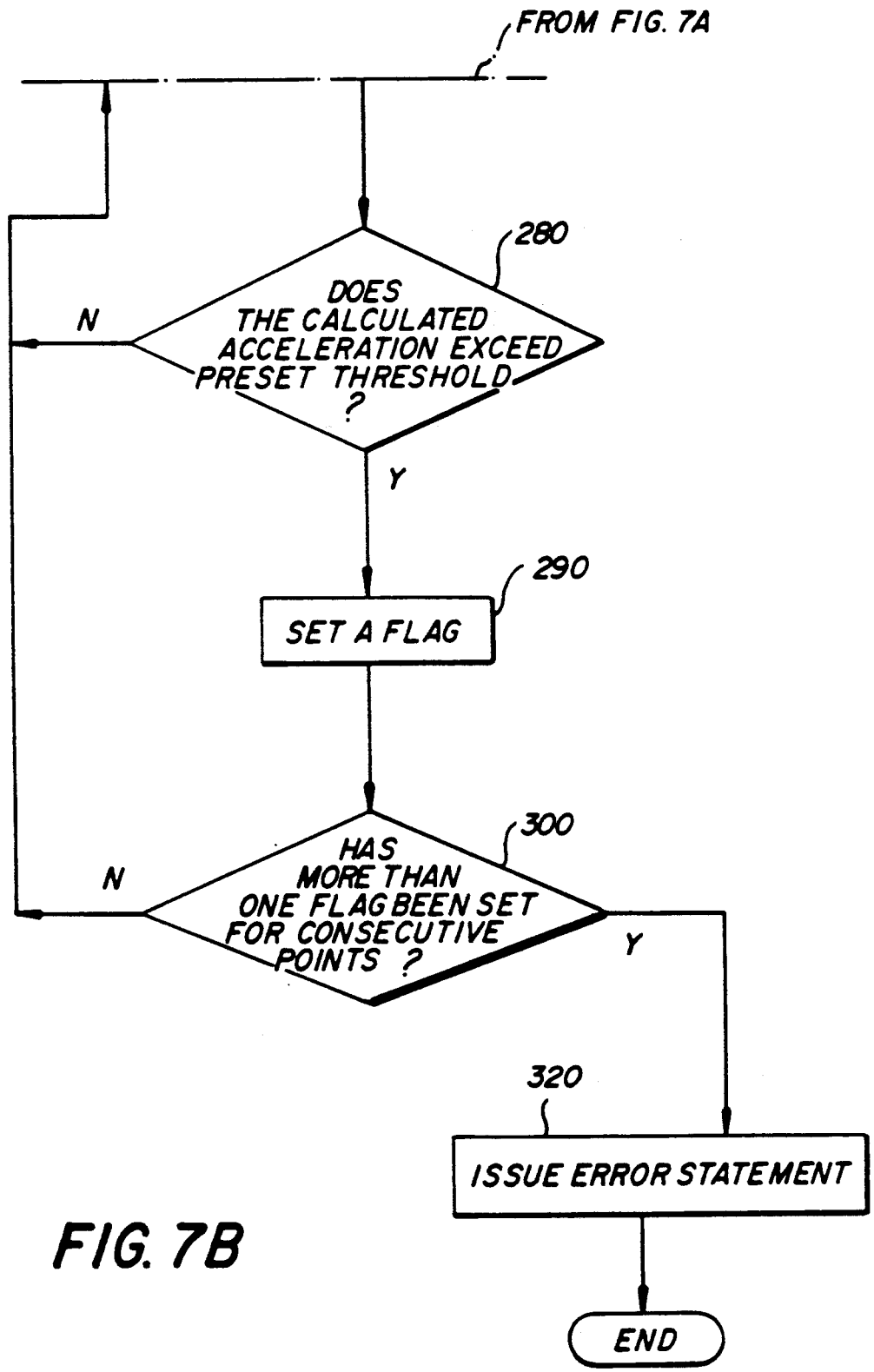

PRESPOT DETECTION METHOD AND APPARATUS IN AN ANALYZER

FIELD OF THE INVENTION

The invention relates to apparatus, such as clinical analyzers, which dispense a drop of sample liquid onto a test element to assay for analytes, and particularly such apparatus that checks for proper dispensing conditions.

BACKGROUND OF THE INVENTION

Wetness detectors are commonly used in clinical analyzers to detect the extent to which patient sample has been dispensed onto a slide-like test element, hereinafter "slide", for analysis. Examples are disclosed in U.S. Pat. No. 4,420,566. Threshold values can be set to cause the detector to flag any slide on which insufficient liquid is dispensed.

Although such a detector has been quite useful, it has not been capable of reliably detecting whether or not a "pre-spot" condition has occurred. That is, the detector has been designed heretofore to detect the desired drop, and not the possible error condition of a "pre-spot". A "pre-spot" occurs if and when the dispenser accidentally drops a quantity of liquid onto the slide prior to the desired dispensing time. If the pre-spot is large enough, e.g., is more than approximately 10% of the desired volume at the time of dispensing, this will adversely affect the slide performance when actual dispensing occurs.

Attempts have been made to use the wetness detector of the aforesaid patent to detect such prespotting. This has been based on an examination of the R-C time decay curve produced by the sensor circuitry. That is, the exponential decay should approach asymptotically an intermediate value, for example 250 A to D "counts". However, any pre-spotting will interrupt the gradual decay of this curve, and the computer can be programmed to detect such interrupts.

Although the concept is clear, in practice it has been difficult to set an absolute value of change in the A/D signal that should represent a pre-spot. The reason is that any absolute value tends to be a function of a particular analyzer. Even the first derivative (i.e., a decrease of say, 24 A/D counts), has not been satisfactory, because of the "noise" that can artificially produce such an effect. More precisely, noise can exist in such analyzer, mostly due to physical motion of the test element relative to the detector, that occurs in the system, which does not represent a pre-spot condition at all.

Thus, prior to this invention it has not been possible to use the wetness-detector to detect pre-spotting, with any high degree of accuracy that will catch all prespots without flagging non-prespots as errors.

SUMMARY OF THE INVENTION

A method and apparatus have been provided that solve the above-stated problems. More specifically, in accord with one aspect of the invention, there is provided a method of detecting improper wetting of a test element by a liquid dispenser using a wetness detector that produces an R-C time decay curve that decreases abruptly in the presence of moisture on the element, the method comprising the steps of a) prior to intended liquid dispensing, generating an R-C time decay signal representing reflectivity of a test element at the absorption band of water, b) for each data point in the signal, calculating the rate of change of the signal over time, c) comparing the calculated rate of slope change for each data point against a threshold noise value representing the rate of change that can be caused by motion of the test element, d) determining if the comparison step c) produces a value greater than the threshold value for two consecutive data points, and e) issuing an error statement in the event step d) finds such two consecutive data points producing a value greater than the threshold.

In accord with another aspect of the invention, there is provided apparatus for detecting improper wetting of a test element by a liquid dispenser using a wetness detector that produces an R-C time decay curve that decreases abruptly in the presence of moisture on the element. The apparatus comprises:

a) means for generating prior to intended liquid dispensing, an R-C time decay signal representing reflectivity of a test element at the absorption band of water, b) means for calculating for each data point in the signal, the rate of change of the signal over time, c) means for comparing the calculated rate of slope change for each data point against a threshold noise value representing the rate of change that can by caused by motion of the test element, d) means for determining if the comparison means c) produces a value greater than the threshold value for two consecutive data points, and e) means for issuing an error statement in the event means d) find such two consecutive data points producing a value greater than the threshold.

Therefore, it is an advantageous feature of the invention that significant pre-spotting of a slide prior to actual drop dispensing can be detected so that such a slide can be flagged and discarded.

It is a related advantageous feature of the invention that such detection can be fine-tuned to eliminate false error flagging due to noise in the system.

Other advantageous features will become apparent upon reference to the following Detailed Discussion when read in light of the attached drawings.

BRIEF SUMMARY OF THE DRAWINGS

FIGS. 5 and 6 are comparative plots similar to those of FIGS. 3 and 4, respectively, but of a dispensing event that is free of any pre-spotting; and FIGS. 7A and 7B are a flow-chart for programming the computer to carry out the invention.

DESCRIPTION OF THE PREFERRED EMBODIMENTS

The invention is described in connection with apparatus used in a clinical analyzer and with certain preferred test elements, hereinafter "slides". In addition, it is useful with dispensing apparatus not part of an analyzer, and with other test elements that contain pre-dried reagents, if it is desired that premature spotting be detected.

Regarding the preferred slides for this invention, they are any of the slides available from Eastman Kodak Company under the trademark "Ektachem".

Figure 1:
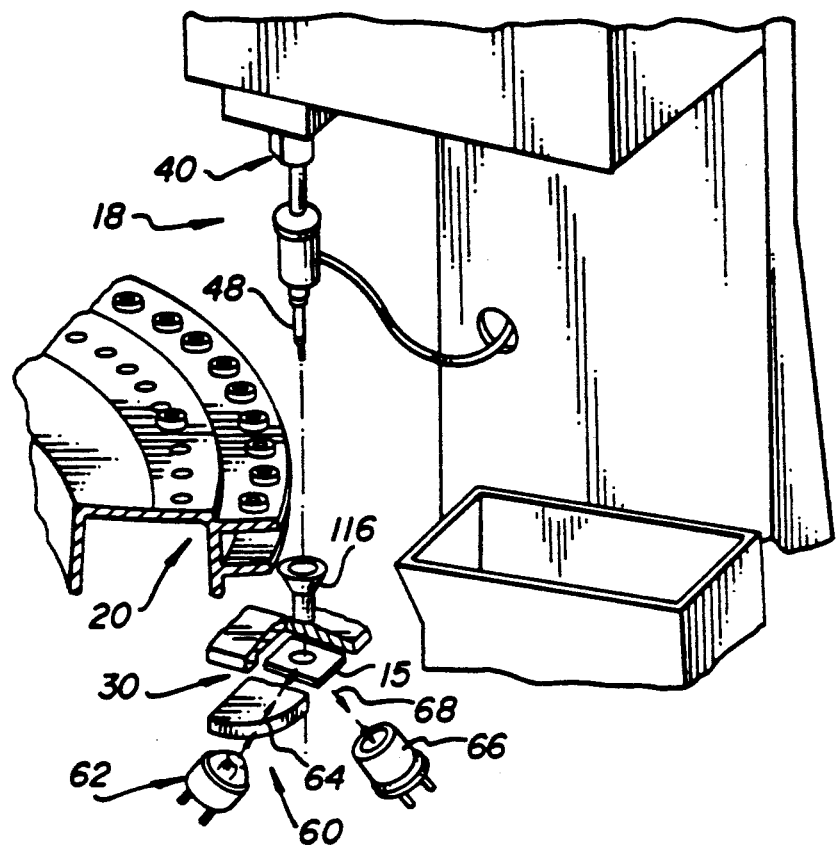
FIG. 1 is an isometric view of an analyzer and its dispensing station, constructed with the wetness detector used in this invention.

A useful environment is a clinical analyzer that has a dispenser station 18, FIG. 1, a source of patient sample such as a tray 20, slide handling means 30, hereinafter a "distributor", for moving a slide into position under dispenser station 18, and a wetness detector 60. The parts of such an analyzer are conventional, and are described in greater detail in U.S. Pat. No. 4,420,566 the details of which are hereby incorporated by reference. Likewise, the wetness detector 60 is so described in that patent. Briefly, it features a light source, e.g., a lamp 62, that projects a beam 64 onto one side of a slide 15, and a sensor 66 that receives reflected radiation, arrows 68, from the slide. Preferably, sensor 66 is a photoelectric cell of the lead sulfide type, equipped with an integral notch filter (not shown) which passes infrared radiation at a wavelength of 1.945 microns. Radiation at a wavelength of 1.945 microns lies within the absorption band of water, contained in a slide 15. Thus, wet slides are characterized by a relatively weak output of the sensor 66 because the radiation is absorbed by the aqueous sample. The sensor 66 and lamp 62 are oriented relative to slide 15 to receive diffuse reflection from slide 15 and to minimize the specular reflection returned to the sensor 66.

Figure 2:
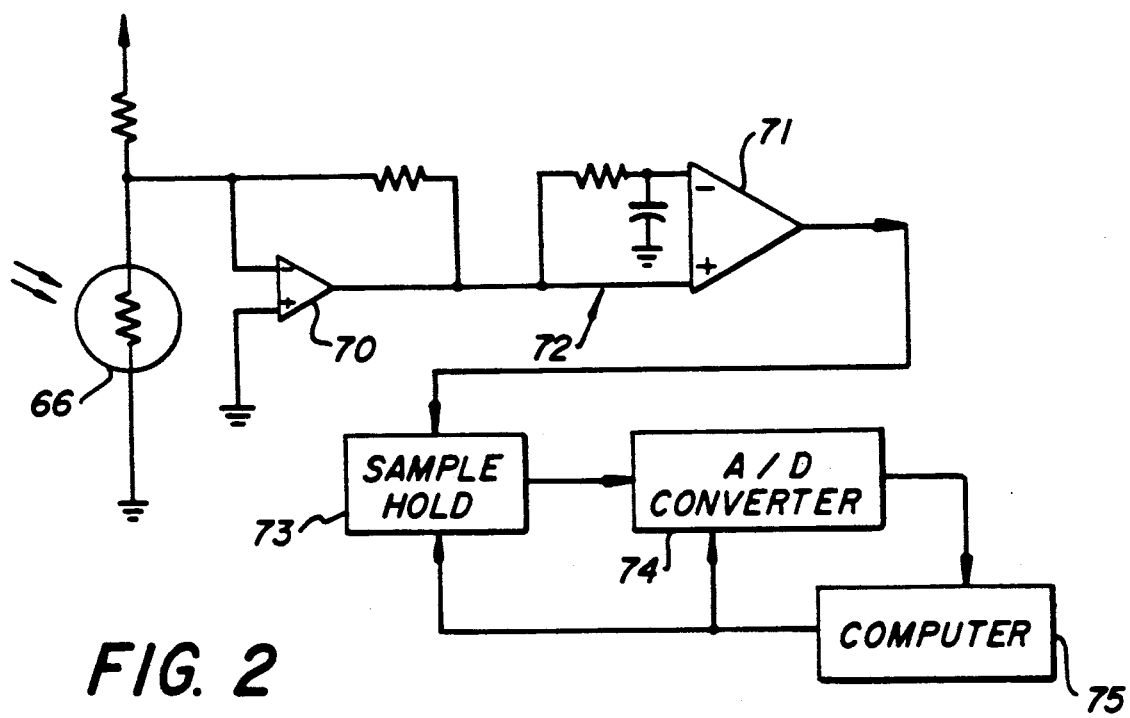
FIG. 2 is a schematic illustration of the circuitry used with the wetness detector.

A useful circuit for operating detector 60 is shown in FIG. 2. This circuit is conventional as it is currently available in analyzers sold by Eastman Kodak company under the trademark "Ektachem 700". The circuit comprises sensor 66, the response of which feeds to an amplifier 70. The output from the amplifier is delivered to a differential amplifier 71 through an R-C circuit 72. The output of amplifier 71 feeds to a sample-and-hold circuit 73, which feeds to an A/D converter 74. The converter delivers digitized data to computer 75 that uses a conventional display (not shown).

Any computing means can be used for computer 75, provided it has enough memory and speed. For example, the microprocessor used for the data storage and manipulation described hereinafter was an Intel 8085.

Referring again to FIG. 1, the "noise" that is generated in the output of sensor 66 that might suggest a pre-spot, but is not, occurs primarily because a tip holder 116 is connected (not shown) to the distributor 30 holding slide 15. When a liquid-dispensing tip 48 is inserted into holder 116 just prior to dispensing the expected drop, misalignment of tip 48 with holder 116 causes some motion of the distributor 30 and thus of slide 15. It is this disturbance of the slide that is detected by sensor 66 as a deviation in the normal R-C decay curve.

Figure 3:
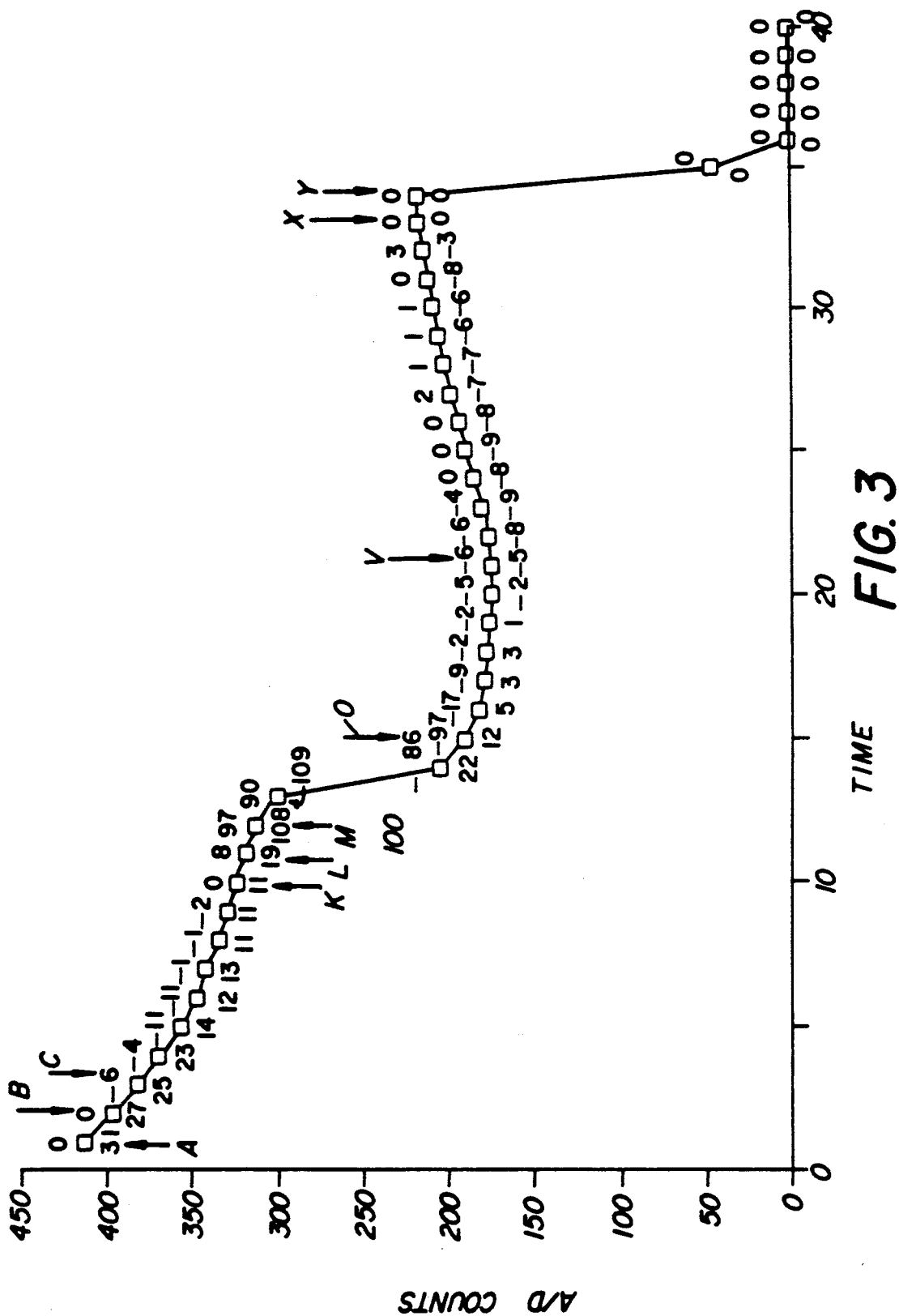
FIG. 3 is a plot of A/D counts produced by converter 74 of FIG. 2, measured over time, and depicting both a pre-spot and the actual, desired drop dispensing.

As noted, the output of converter 74 is an R-C decay to provide an auto-zeroing function. A representative output appears in FIG. 3. This data was obtained using an analyzer supplied by Eastman Kodak Company under the trade name "Ektachem 500" analyzer. The abscissa is a time scale of arbitrary units, for example, units spaced apart about 25 microsec. The ordinate is the A/D counts from the converter. Readings are taken of the converter output every one of these units, and stored in the computer. Preferably, the entire data sequence is produced and then stored, before any analysis occurs. Alternatively, however, real-time processing of the data can occur if followed within the limits of the flow chart described hereinafter.

The numbers appearing above and below curve 100 of the plot are as follows: The numbers below represent the difference in value of the A/D count, from the point in question, and the value two data points thereafter, hereinafter the "look-ahead" change. Thus, comparing point A with point C, there is a decrease in A/D count of about 31 over that period. With the exception of data points A and B, and X and Y, the numbers above the curve 100 represent the difference (i.e., the second derivative) between the look-ahead change at that point, and the change in A/D count looking back two data points, hereinafter the "look-back" change. As will be readily apparent, the "look-back" change is in fact the "look-ahead" change listed below at the data point that is two previous to that.

(Two data points for the "look-ahead" and "look-back" have been selected as being more representative of the curve behavior.)

For example, point M has a look-ahead change of 108, and a look-back change of 11, so that the acceleration represented by point M is 97 (from 108–11).

Data points A and B, and X and Y, are treated differently, in that for A and B, there is no "look-back" value obtainable. Similarly, for points X and Y there is no "look-ahead" value since they are the last two values on curve 100. Accordingly, the acceleration is not determined for these.

Taking a broader view of curve 100, it will be seen that the portion from point A to point C is a fairly typical R-C decay curve. But from point M to point O, an unusual event occurred. Thereafter, the change in the curve is much less pronounced, until point Y is encountered. That is the time at which normal drop dispensing occurs, as is detectable by the sharp drop in the A/D count. (The upswing in curve 100 occurring between point V and point Y is an artifact and is due to the fact that the prespot moved the curve below nominal and the R-C circuit is driving the curve to the nominal value.)

Figure 4:
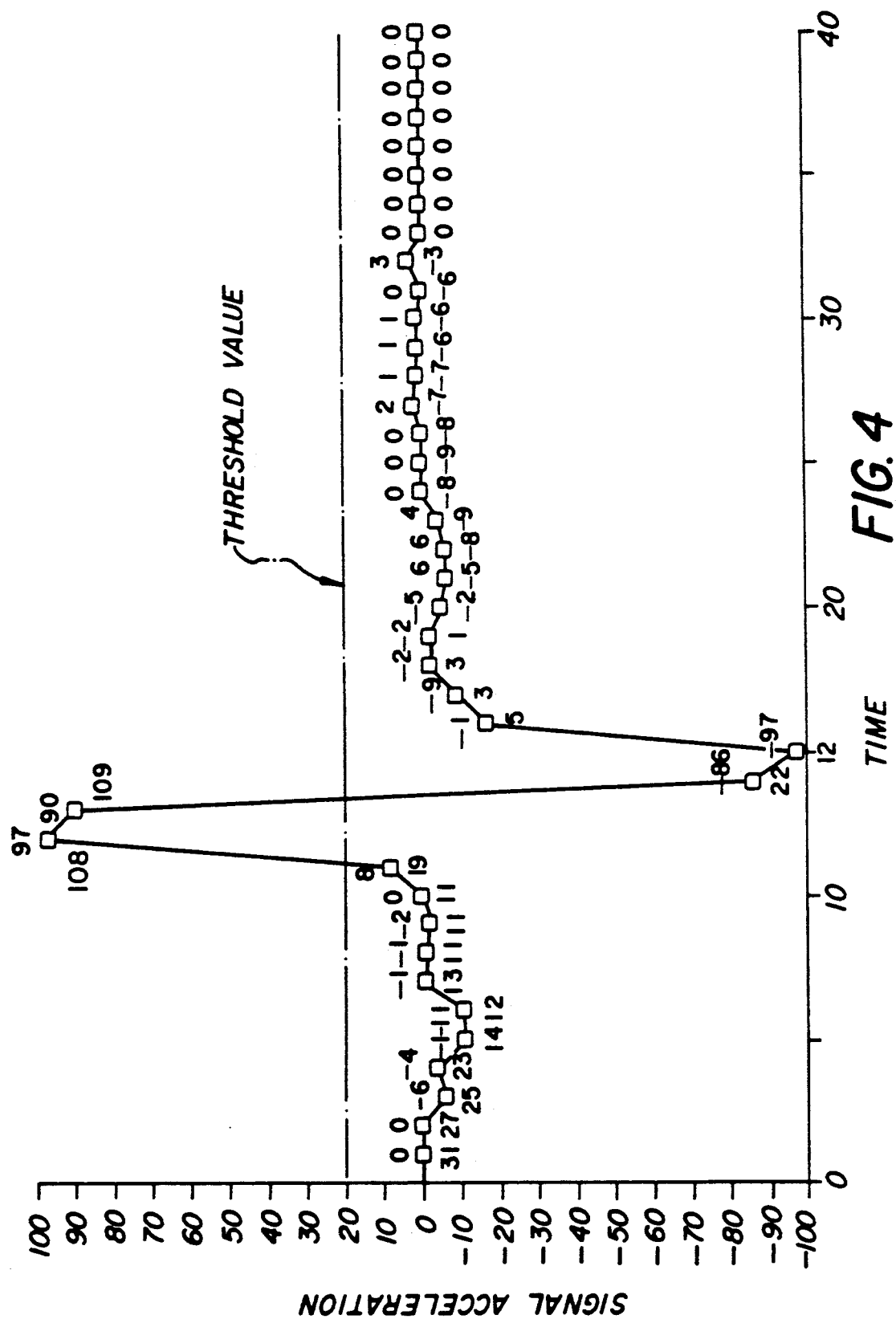
FIG. 4 is the second derivative plot of the values that appear in FIG. 3.

The question then is, was the change represented by point M to point O, a pre-spot, or noise due to, e.g., slide motion. The second derivative is plotted to determine this, as is shown in FIG. 4. The values for the points in time correspond exactly to the values posted above those times in the plot of FIG. 3.

Only the positive second derivatives are considered, since negative changes are the norm for an R-C decay curve. Most specifically, a threshold value of +20 has been set as shown, for reasons discussed below. In accord with the invention, there must be at least two readings taken with second derivative values above this threshold, to signal an error due to prespotting. This in fact is present in FIG. 4. At least two such readings are preferred because they insure that the change occurring is sufficiently prolonged as to represent a real event rather than "noise".

Independent observation of station 18 (FIG. 1) revealed that, in fact, a pre-spot had occurred at time M through time 0, of about 1 μL. Such an amount is more than necessary to unacceptably alter the course of a reading taken on an "Ektachem" slide using the desired dispense drop size of about 10 μL.

The threshold of 20 is selected as a function of the analyzer. This particular analyzer can produce motion of the slide and other noise that will create a disturbance in the R-C signal that gives a second derivative that produces no, or at most one, value above 20. A different threshold may be appropriate for other analyzers. One can readily ascertain the threshold value for a given analyzer in the following manner: At least several hundred nominally correct dispensings are done under no "pre-spot" conditions, and the A/D counts are observed, particularly the deviations from the expected R-C decay curve that are caused by any noise, such as mechanically induced motion of the slide. These deviations are then statistically analyzed, and the 95% confidence level is established as to what A/D count is needed to exceed the probability that the deviation was "noise".

Figure 5:
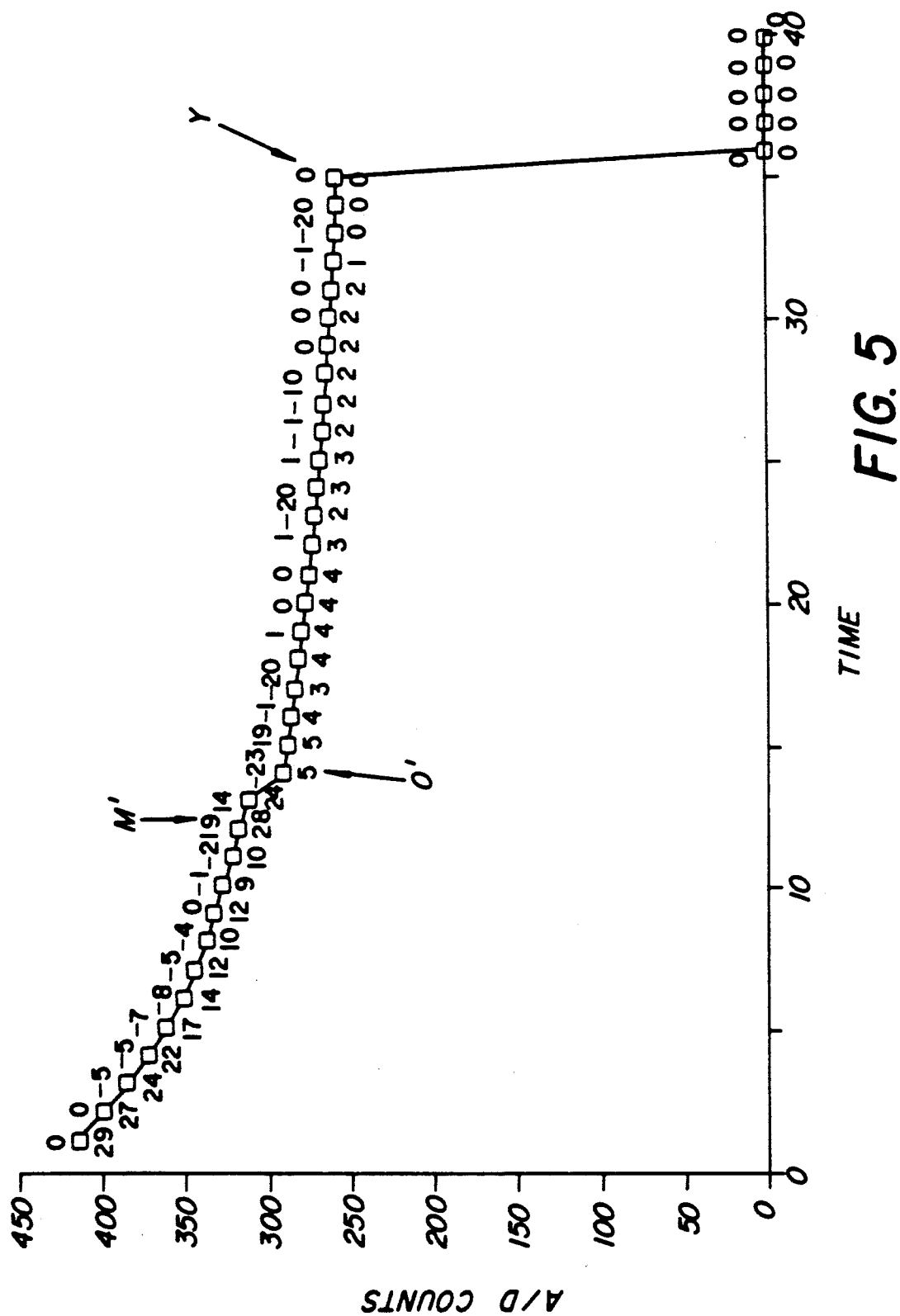

That the value of 20 is in fact useful for this analyzer can be seen in the plots of FIGS. 5 and 6. The A/D count therein depicted occurred as distributor 30 was in fact jarred as described, during the time of point M' through point O'. Otherwise curve 100' is an excellent R-C decay curve leading to the desired drop-dispensing at point Y. By actual observation, it was determined that NO pre-spotting occurred at this time. FIG. 6 illustrates that the second derivative had only two high positive values, 19 and 14, and these are short of the 20 threshold value.

Figure 7A:
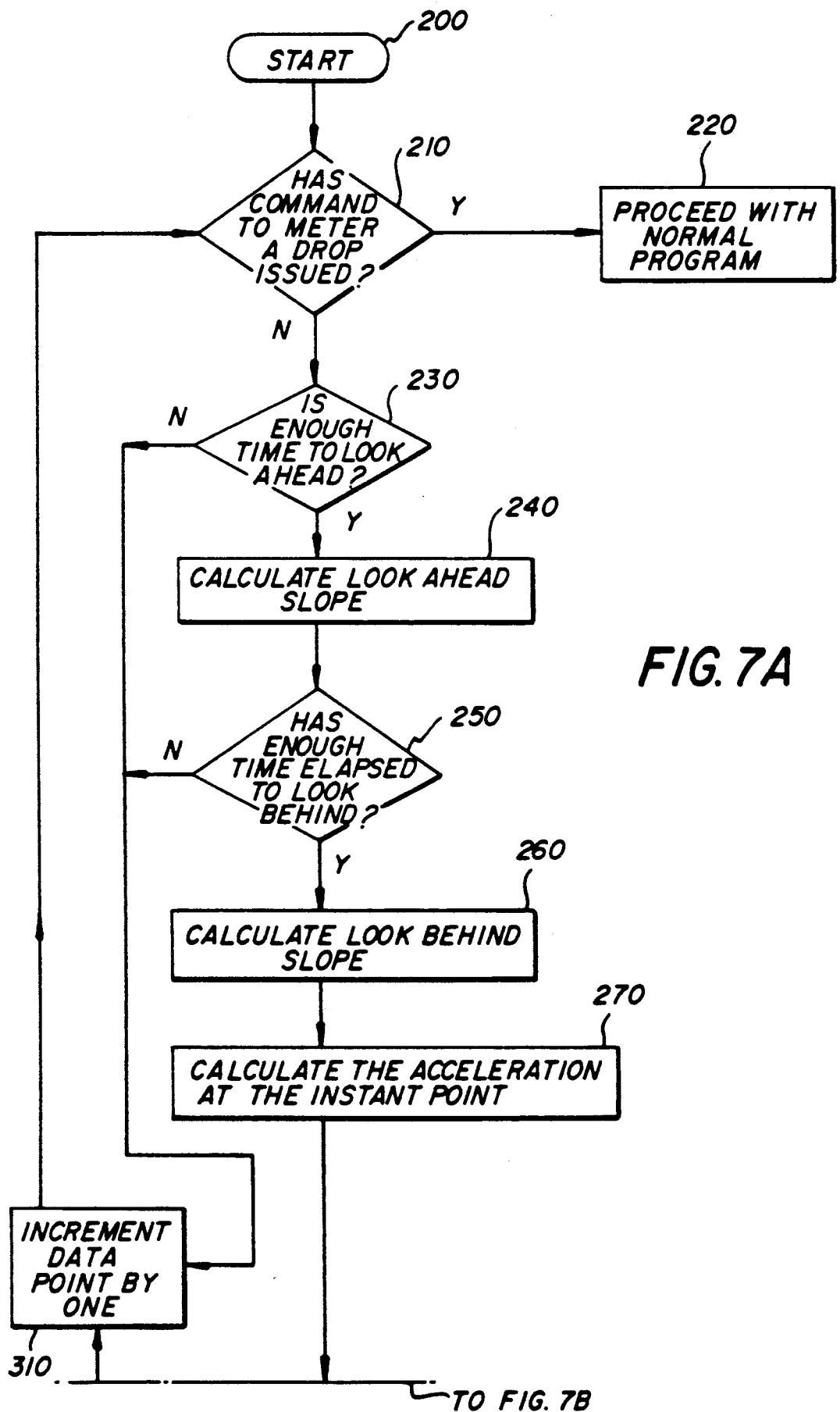

Computer 75 is programmed in any conventional way to carry out the steps of the invention described above. The programming will be apparent from the previous description. A useful summary of the programming is set forth in FIG. 7. The program starts, step 200, with the conversion of data from analog to digital counts at converter 74. Next, step 210, the computer checks at any given data point, herein the "instant point", to determine if the command to dispense or meter a drop at station 18 from tip 48 has been issued. If yes, the usual program 220 takes over, which includes a subroutine for normal drop detection. If no, the computer interrogates, step 230, to determine if there is enough time to do a "look ahead" slope, i.e., is the data point in question a point before the point corresponding to points X and Y on curve 100? If no, the data point is ignored and the process proceeds with an evaluation of the next data point. (Points A, B, X, Y are at times when prespot occurrence is very unlikely.) If yes, then step 240 proceeds with the calculation of that "look-ahead" slope, which is simply the subtraction of the A/D counts of the data point that is 2 points after the instant point, from the A/D count at the instant point. Next, step 250, the computer interrogates to see if enough data points have occurred to do the "look-behind" slope— that is, is the instant point beyond the point corresponding to point B on, e.g., curve 100? If no, then the data point is ignored and the next data point is evaluated. If yes, then step 260 proceeds, which is the calculation of the look-behind slope. This is simply the subtraction of the A/D count for the instant point from that of the data point that is two data points previous. Next, step 270, computer 75 calculates the acceleration at the instant point, which is simply the subtraction of the look-behind slope from the look-ahead slope for the instant point. After this, an "if-then" command, step 280, interrogates whether the calculated acceleration exceeds a preset threshold value stored in the computer 75. If yes, then a first flag is set, step 290, and the program goes to step 300 which interrogates to see if more than one such flag has been set for 2 consecutive points. If no, the computer simply executes step 310. Once step 310 is executed, the program returns to step 210. At this point, the process is a simple reiteration of the steps already enumerated, until the interrogation at step 300 produces a "yes". In that case, step 320, an error statement is issued. Such an error statement, among other things, interrupts the processing of the slide in question so that either it is discarded and not completely processed to the "read" station (not shown). If the slide with the prespot is read for a value, that value is either not posted to the user or is posted as being in error.

Repeats of the assay of the erroneous slide are done simply by obtaining a fresh slide in distributor 30 that duplicates the prespotted test element, and dispensing from tip 48 a fresh drop of patient sample onto that fresh slide.

The invention has been described in detail with particular reference to preferred embodiments thereof, but it will be understood that variations and modifications can be effected within the spirit and scope of the invention.

What is claimed is:

1. A method of detecting improper wetting of a test element by a liquid dispenser using a wetness detector that produces an R-C time decay curve of reflectivity measured using an absorption wavelength of water that decreases abruptly if moisture is present on the element, the method comprising the steps of:
   a) prior to intended liquid dispensing, generating an R-C time decay signal of data points representing reflectivity of a test element at said absorption wavelength of water,
   b) for each data point in said signal, calculating an estimated first and second derivative of said signal over time,
   c) comparing said second derivative for each data point against a threshold noise value representing the second derivative caused by motion of a test element,
   d) determining if comparison step c) produces a value greater than said threshold value for two consecutive data points,
   e) issuing an error statement if step d) finds such two consecutive data points producing a value greater than said threshold, and
   f) redoing the assay of the test element in the event step e) results in the execution of an error statement.

2. A method as defined in claim 1, wherein said step b) comprises calculating the rate of change measured over two data points actually detected.

3. A method as defined in claim 1 or 2, and further including in step a) the step of storing said decay signal, and wherein said step b) is undertaken on said stored data points after the dispenser dispenses a desired drop.

4. Apparatus for detecting improper wetting of a test element by a liquid dispenser using a wetness detector that produces an R-C time decay curve of reflectivity measured using an absorption wavelength of water that decreases abruptly if moisture is present on the element, said apparatus comprising:
   a) means for generating prior to intended liquid dispensing, an R-C time decay signal of data points representing reflectivity of a test element at said absorption wavelength of water,
   b) means for calculating for each data point in said signal, an estimated first and second derivative of said signal over time, c) means for comparing said second derivative for each data point against a threshold noise value representing the second derivative caused by motion of the test element,
d) means for determining if said comparison means c) produces a value greater than said threshold value for two consecutive data points,
e) means for issuing an error statement if means d) find such two consecutive data points producing a value greater than said threshold, and
f) means for redoing the assay of the test element, if means e) results in an error statement being issued.

5. Apparatus as defined in claim 4, and further including means for storing the signal generated by said generating means a).

* * * * *